(12) United States Patent
Eide et al.

(10) Patent No.: US 11,724,001 B2
(45) Date of Patent: Aug. 15, 2023

(54) AIR PURIFICATION AND STERILIZATION UNIT

(71) Applicant: AERUS MEDICAL, LLC, Dallas, TX (US)

(72) Inventors: Andrew Eide, Rockwall, TX (US); Christopher Carroll Kyte, Elizabeth, TN (US); Joseph P. Urso, Dallas, TX (US); Deborah Jessup, Pittsburgh, PA (US)

( * ) Notice: Subject to any disclaimer, the term of this patent is extended or adjusted under 35 U.S.C. 154(b) by 104 days.

(21) Appl. No.: 17/155,080

(22) Filed: Jan. 21, 2021

(65) Prior Publication Data

US 2021/0228762 A1     Jul. 29, 2021

Related U.S. Application Data

(60) Provisional application No. 62/964,845, filed on Jan. 23, 2020.

(51) Int. Cl.
     *A61L 9/20*        (2006.01)

(52) U.S. Cl.
     CPC .......... *A61L 9/205* (2013.01); *A61L 2209/12* (2013.01); *A61L 2209/14* (2013.01)

(58) Field of Classification Search
None
See application file for complete search history.

(56) References Cited

U.S. PATENT DOCUMENTS

| | | |
|---|---|---|
| 2012/0089209 A1 | 4/2012 | Schoenbach et al. |
| 2012/0316656 A1 | 12/2012 | Amos et al. |
| 2015/0231298 A1* | 8/2015 | Eide .................. B01D 53/885 |
| | | 422/122 |
| 2016/0212853 A1 | 7/2016 | Kang |
| 2017/0227177 A1 | 8/2017 | Tiwari et al. |
| 2018/0224134 A1 | 8/2018 | Bae et al. |
| 2018/0250431 A1 | 9/2018 | Eide et al. |

FOREIGN PATENT DOCUMENTS

| | | | |
|---|---|---|---|
| CN | 105042709 A | * 11/2015 | ............... A61L 9/20 |

OTHER PUBLICATIONS

Gao, T. CN105042709A—translated document (Year: 2015).*
International Search Report and Written Opinion received for PCT Patent Application No. PCT/US21/14678, dated Apr. 16, 2021, 10 pages.

* cited by examiner

*Primary Examiner* — Jelitza M Perez
(74) *Attorney, Agent, or Firm* — Workman Nydegger; Logan Christenson; John Guynn

(57) ABSTRACT

Disclosed is an air purification device having a housing for holding a photocatalytic oxidation (PCO) unit and a fan assembly. The device may also optionally include a filter compartment for holding a filter such as a HEPA filter. The air purification device is configured to provide effective purification and sanitation of air in a targeted indoor environment, and in particular in a medical environment such as a hospital.

18 Claims, 6 Drawing Sheets

AIR PURIFICATION AND STERILIZATION UNIT

CROSS-REFERENCE TO RELATED APPLICATIONS

This application claims priority to and the benefit of U.S. Provisional Patent Application Ser. No. 62/964,845, filed Jan. 23, 2020 and titled "Air Purification and Sterilization Unit", the entirety of which is incorporated herein by this reference.

BACKGROUND

Conventional systems for treating ambient air and removing airborne particles include high-efficiency particulate air (HEPA) filtration systems. These systems utilize filters that are required to meet certain HEPA requirements, such as the ability to remove 99.97% of particles with diameter greater than or equal to 0.3 µm in air passing through the filter(s). While HEPA filtration systems may be useful for removing particles from the air, they suffer from all the limitations common to filtration systems, such as filters that clog over time and require continual monitoring and replacement. Filtration-based systems are also incapable of deactivating chemicals, removing unwanted gases, or removing smaller odor-causing molecules. Moreover, while a HEPA filtration system can remove several airborne contaminants, it will not treat nearby surface contaminants.

Other systems may utilize activated carbon filters or electrostatic filters. While these may be utilized to enhance the ability to trap contaminants and improve the effectiveness of filtration, they still involve the above-mentioned limitations common to filtration-based systems such as filter replacement, degrading filter performance over time, and the inability to treat surface contaminants.

Other air purification systems, commonly referred to as "ionizers," are designed to emit negative ions into the surrounding air. These ions attach to positively charged contaminants such as pollen and dust. The contaminants then become weighed down and are more likely to settle or are easier to trap in a collection plate. However, because many of the contaminants are simply moved to the floor or walls rather than destroyed or removed, they can reenter the air after the negative ions dissipate or disassociate. If a collection plate is used, it must be regularly cleaned or replaced as with any filtration system.

Other air purification systems are designed to use ultraviolet (UV) radiation to inactivate and/or degrade airborne contaminants. These systems may be referred to as UV germicidal irradiation or UVGI air purifiers. The UV light is typically tuned to short-wave UV light (UV-C light). In operation, air is directed through the system and past one or more UV lamps, with the intent of using the UV light to directly disinfect the passing air. Although UVGI systems are capable of destroying some contaminants rather than trapping/filtering all passing contaminants, they have limitations. For many bacteria and mold contaminants, especially spores, the brief exposure to UV light is not enough to effectively destroy the contaminant. Some volatile organic compounds (VOCs) may also be resistant to UV energy, or worse, be reactive with UV light in a way that makes them more harmful or exposed to nearby individuals.

Photocatalytic oxidation (PCO) air purifiers are somewhat similar to UV air purification systems in that they also utilize UV light. However, rather than using the UV light to directly interact with passing contaminants, PCO systems direct UV light onto a catalyst material. Water molecules in the ambient air then interact with the UV light and the catalyst to generate a variety of oxidizers such as hydroxyl radicals. The oxidizers can then attack organic molecule contaminants and degrade them into less harmful substances.

Thus, rather than trapping contaminants, PCO systems are capable of destroying and removing contaminants from the treated environment. However, conventional PCO systems have several limitations. For example, the passing air must be brought into sufficient proximity with the catalyst for the generated oxidizers to mix with the air and contact contaminants in the air. Ideally, a portion of the generated oxidizers should also continue to pass beyond the catalyst and UV lamp so that oxidizers can reach nearby surfaces and provide treatment of surface contaminants as well.

Several design decisions must therefore be made as to where to position the catalyst material and the UV assembly relative to each other and relative to the airflow path. If there is insufficient contact between passing air and the catalyst material, or if there is insufficient irradiation of the catalyst material, there will be reduced generation of oxidizers, poor mixing of the oxidizers with the air, or both, ultimately leading to suboptimal treatment of the contaminants. On the other hand, excessive contact between the catalyst and the airflow path and/or between the UV assembly and the airflow path may unnecessarily restrict airflow, which can increase the operational power demand needed to run the system and/or reduce the volumetric airflow through the system. Reduced airflow can hamper the treatment effectiveness of the system, increase the time it takes to clean the targeted environment, and/or hinder the ability of the system to emit oxidizers very far beyond the catalyst where they can treat surface contaminants.

Accordingly, there is an ongoing need for improved PCO-based air purification systems. An effective air purification unit should be capable of readily providing treatment and purification of ambient air.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Introduction

Exemplary air purification devices are described herein. In one embodiment, an air purification device includes a housing for containing a PCO unit and a fan assembly. The device may also optionally include a filter compartment for holding a filter such as a HEPA filter. As described in more detail below, the air purification device is configured to provide effective purification and sanitation of air in a targeted indoor environment.

The air purification devices described herein may be particularly beneficial for purifying and sanitizing air in a medical environment, such as a hospital room, emergency room, operating room, doctor's office, examination room, recovery room, nursery, and the like. The air purification units described herein may therefore beneficially reduce or prevent the occurrence of nosocomial infections. The combination of HEPA filtration and PCO activity work to remove contaminants (via filtration) and destroy/kill remaining contaminants/pathogens (via oxidizers generated by the PCO unit). Carbon filters and/or ionizers may optionally be added as well to further enhance air purification effectiveness.

The positional descriptors "upper," "lower," "right," "left," "front," "back," "forward," "backward," "vertical," "horizontal," "lateral," and the like are used for convenience in describing the relative positions of the different components of the air purification devices described herein. However, it will be understood that the operation of the components of the device 100, including the PCO unit, are not necessarily orientation dependent, and thus in some applications the "lower" side will not necessarily be facing in the direction of gravity, and the longitudinal axis of the PCO unit need not necessarily be orthogonal to the ground, for example.

Embodiments described herein may also be capable of providing enhanced overall performance as compared to conventional systems or systems not having the same structural features and/or optimizations. The term "enhanced overall performance," as used herein, means the ability to better remove contaminants from a given room/environment on a power basis (e.g., per watt used by the device), a per volume basis (e.g., per cm$^3$ taken up by the device), or both, as compared to a device not having the same features and/or optimizations.

Air Purification Device Overview

Figure 1:
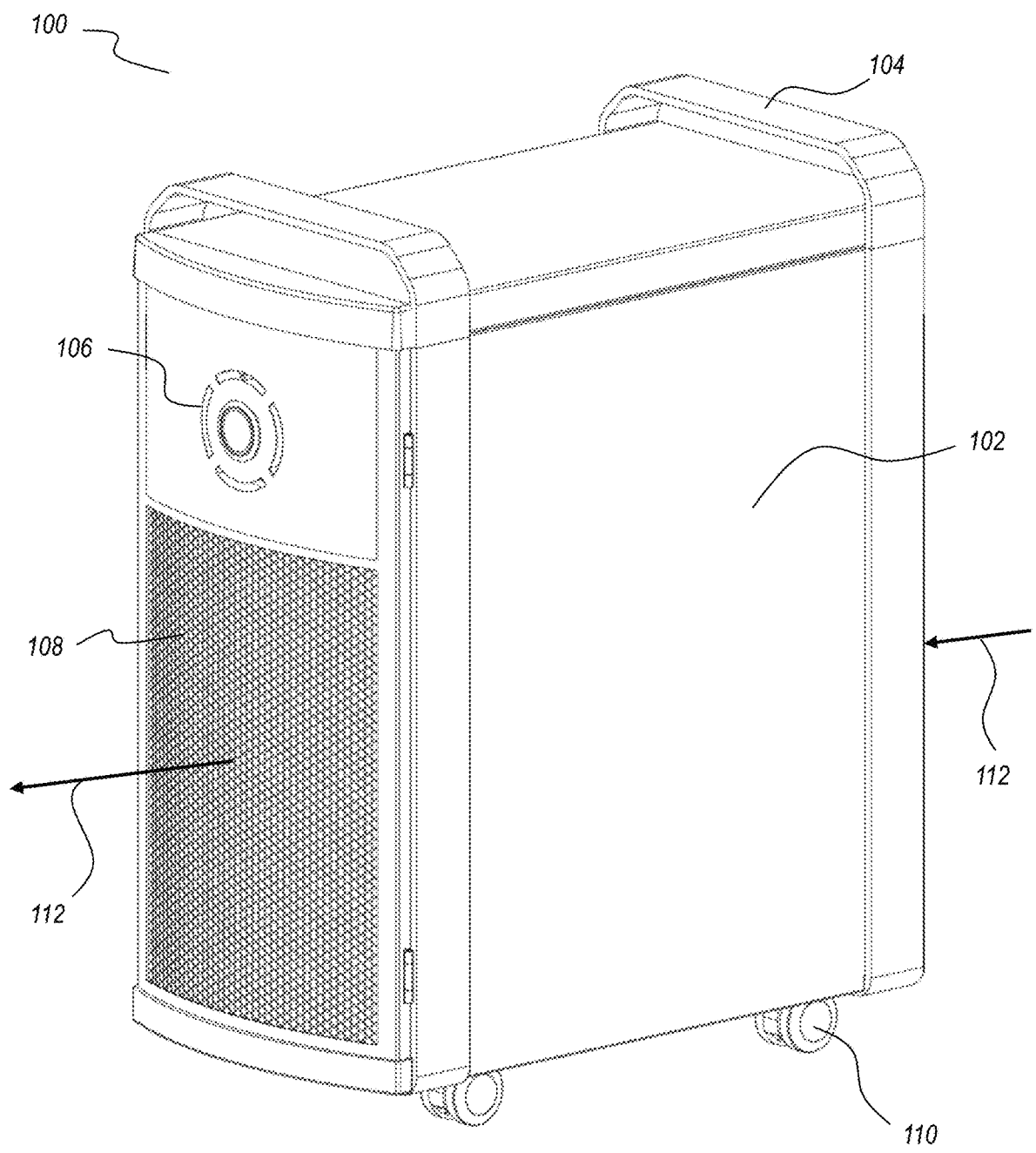
FIG. 1 illustrates a perspective view of an exemplary air purification device.

FIG. 1 illustrates an isometric view of an exemplary air purification device 100. The illustrated air purification device 100 includes a housing 102 in which other components, explained in greater detail below, are contained. The housing 102 provides protection from internal components of the device 100 such as moving parts (e.g., fan) and emanating ultraviolet light (e.g., from the internal PCO unit).

The housing 102 may include one or more handles 104 to allow the device 100 to be moved to a desired location. Such handles 104 may extend along the upper side of the housing 102, as shown, and/or may be located along the side of the device 100 and/or at other suitable locations. The housing 102 may also include a set of wheels 110 (e.g., caster wheels) to enable easier movement and positioning to a desired position.

The air purification device 100 may also include a user control 106, which may include an indicator light, fan speed control, timer, power button(s), or combination thereof. An outlet 108 allows air to flow outward into the ambient environment following treatment and purification within the device 100. An inlet 109 (see FIG. 2) may be positioned on the opposite side of the unit 100 for receiving air from the ambient environment. Air thus flows through the device 100 in the direction indicated by arrows 112.

Figure 2:
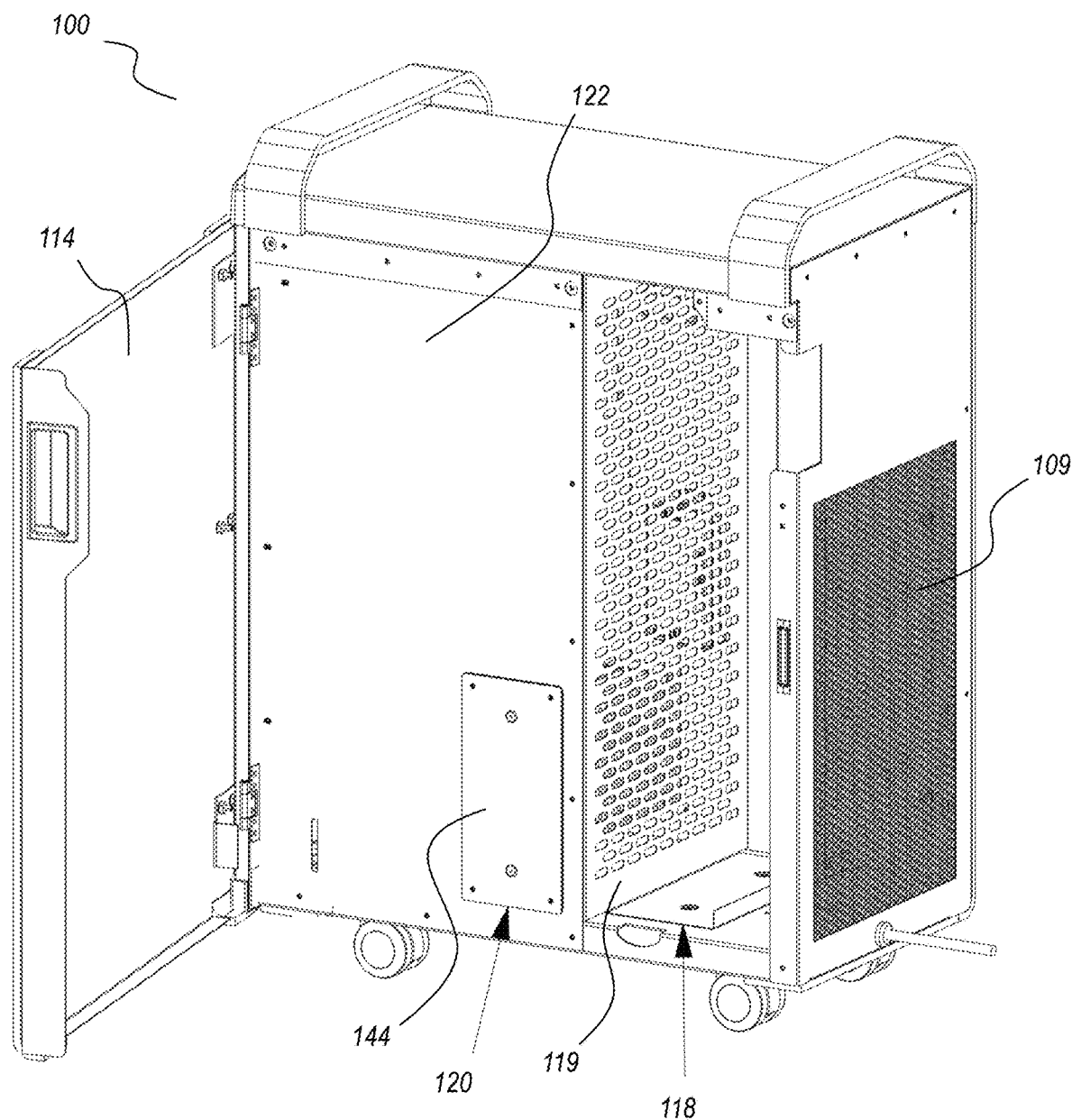
FIG. 2 illustrates the air purification device of FIG. 1 with an access door in an open position to illustrate certain internal features of the device.

FIG. 2 illustrates the air purification device 100 in a partially open position. As shown, part of the housing 102 may be formed as a door panel 114 which may be selectively opened/shut by manipulating a door handle 116 to allow the door panel 114 to swing open/shut. The door panel 114 may be opened to reveal a filter compartment 118 and an inner panel 122. The PCO unit 120 may partially extend through the inner panel 122 to allow access for servicing and/or replacement.

The filter compartment 118 is configured in size and shape to receive one or more air filters such as, preferably, a HEPA filter. One or more other types of filters, such as carbon filters, may additionally or alternatively be used. A grating 119 may be positioned to separate the filter compartment 118 from the remaining internal compartment of the unit 100. The air filter, when positioned within the filter compartment 118, thus sits between the inlet 109 and the other internal components of the device, including the PCO unit 120 and the fan. The filter may be readily inspected and/or replaced by opening the door panel 114, without the need to further open the device 100 or cause the user to be exposed to the other components of the internal compartment.

The device 100 may therefore be operated to combine the functions of HEPA filtration with PCO activity to more effectively purify the air of a targeted environment. By using filtration prior to passing the air into the PCO unit, relatively larger contaminant particles may be filtered, while unfilterable particles or those that get through the filter are then exposed to oxidizers generated by the PCO unit. This, in effect, leads to a higher relative concentration of oxidizers to contaminants and increases overall purification ability of the device 100.

Figure 3:
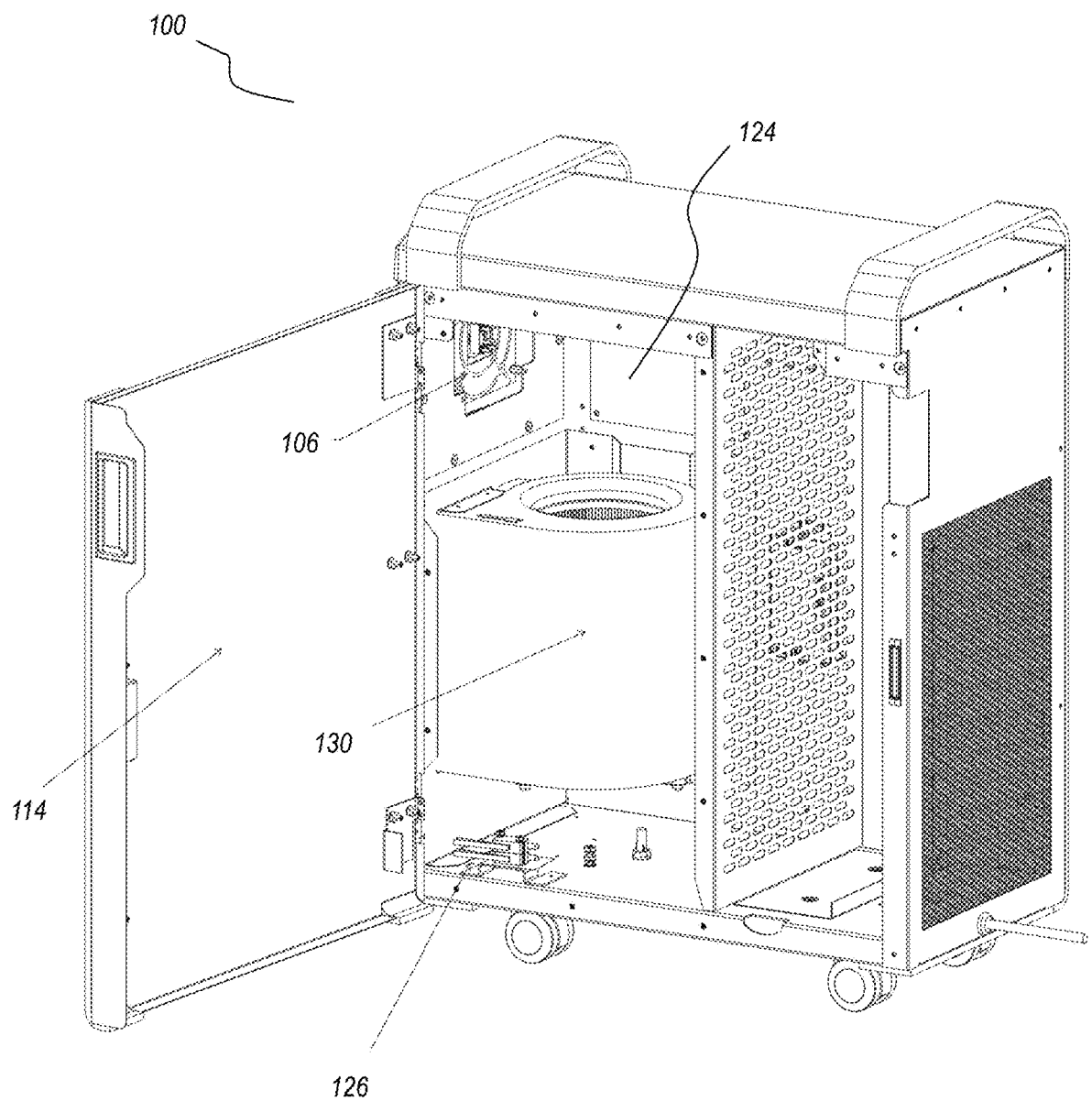
FIG. 3 illustrates the air purification device of FIG. 2 with an internal panel removed to illustrate additional internal features of the device.

FIG. 3 illustrates the air purification device with the internal panel 122 removed in order to better visualize some of the components of the internal compartment 124. The device 100 may include one or more safety switches 126 (e.g., proximity sensors, mechanical sensors, etc.) that prevent operation of internal components when the internal panel 122 is not in proper position. The one or more safety switches 126 may be configured, for example, to prevent operation of the fan assembly 130 and/or the ultraviolet lamp(s) of the PCO unit 120.

The fan assembly 130 is coupled to the outlet 108 and is configured to move air from the internal compartment 124 out through the outlet 108. The fan assembly 130 preferably includes a centrifugal-type fan that receives air near the axis/shaft of the fan and moves it in a direction substantially perpendicular to the axis/shaft. In the illustrated embodiment, for example, air from underneath (and/or above) the fan assembly 130 enters along the axis of the fan and is moved outward through the outlet 108.

In the illustrated embodiment, the axis of the fan is oriented vertically, though other embodiments may position the axis horizontally or at some other suitable angle. The PCO unit 120 is not visible in the view of FIG. 3, but is preferably generally positioned upstream of the fan assembly 120, as will be apparent from the discussion related to FIG. 4. One or more other types of fans may additionally or alternatively be included, such as an axial-flow fan or cross-flow fan.

Figure 4:
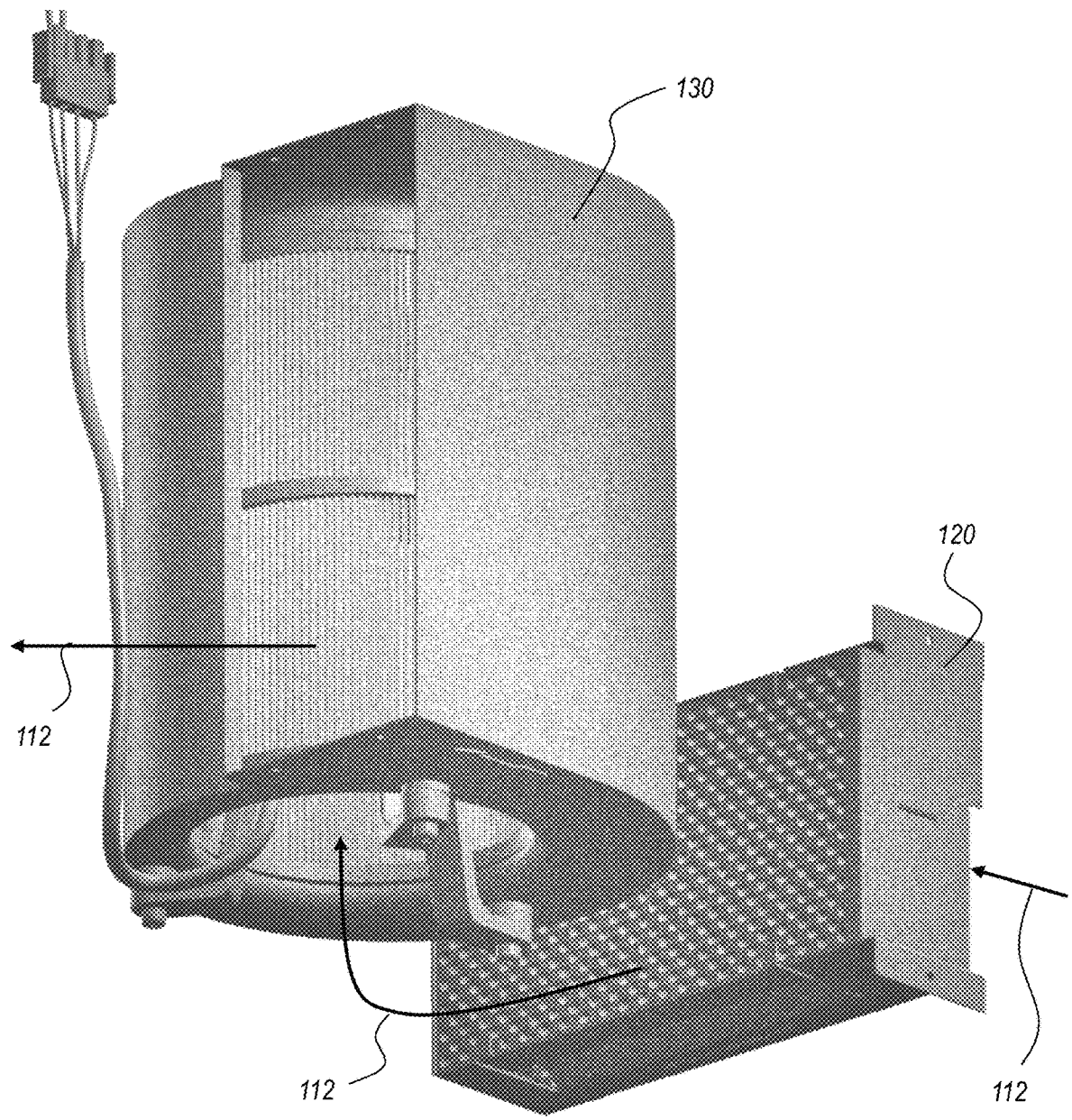
FIG. 4 illustrates a PCO unit and fan assembly of the air purification device.

FIG. 4 illustrates a bottom perspective view of the PCO unit 120 and fan assembly 130, with the other components of the device removed to better view these components. Arrows 112 indicate the air flow path (though some air may also enter the fan assembly 130 from the upper side). As explained in greater detail below, the PCO unit 120 operates to generate oxidizers which are mixed with the passing air. These oxidizers may then act to destroy contaminants present in the passing air. At least some oxidizers may also pass out of the device 100 to move beyond the device 100 and into the targeted environment. Such oxidizers may then come into contact with surfaces within the targeted environment to provide sanitizing action on such surfaces.

Photocatalytic Oxidation Unit

Figure 5:
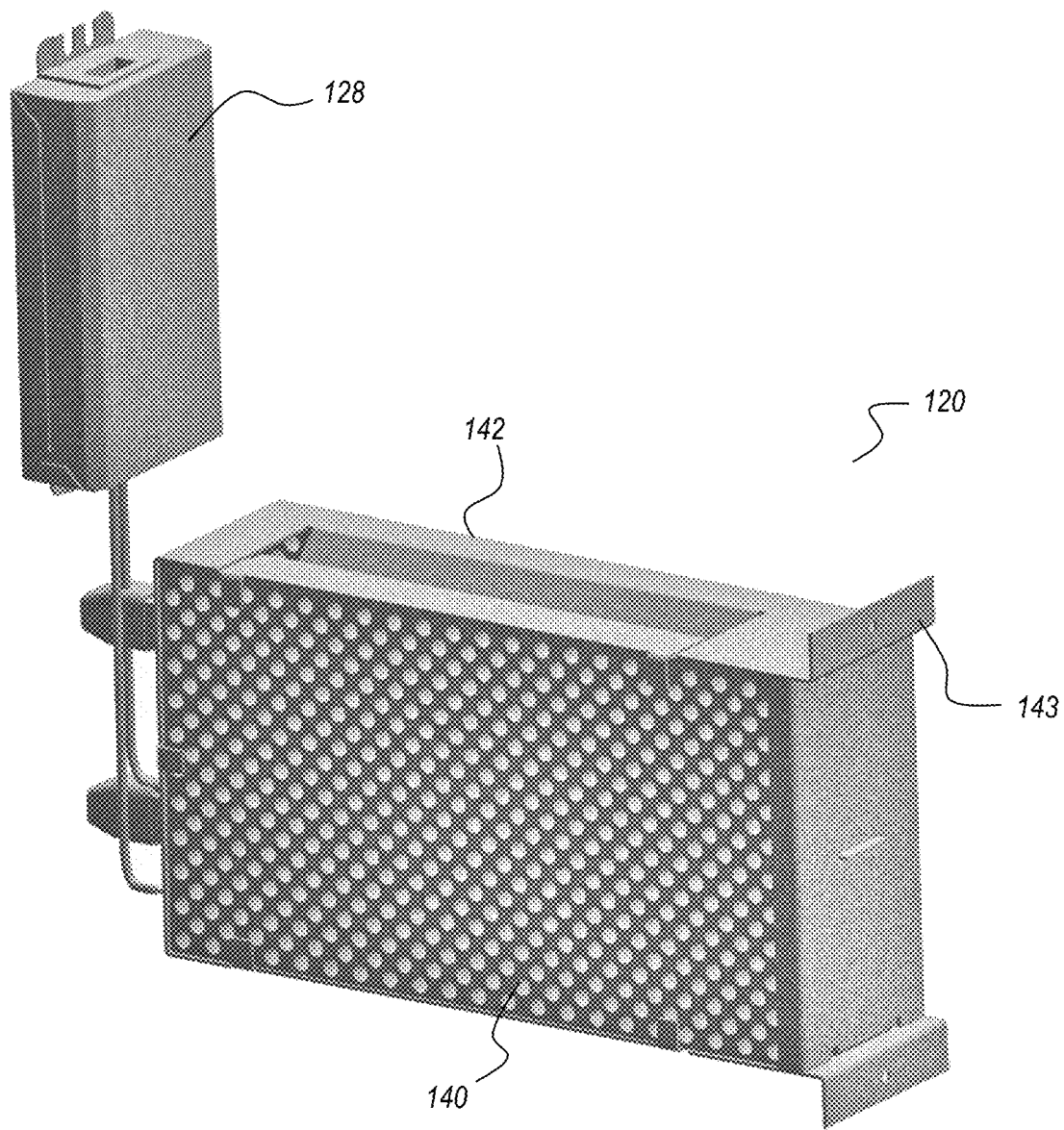
FIG. 5 illustrates a detailed view of the PCO unit.

FIG. 5 is a detailed view of the PCO unit 120. The PCO unit 120 is operatively coupled to a ballast 128. The ballast 128 may include electronic circuitry for controlling power delivery to one or more ultraviolet lamps of the PCO unit 120. The PCO unit 120 includes a frame 142 configured to provide structure for supporting and orienting the one or more ultraviolet lamps and one or more photocatalytic cell panels 140. The frame 142 may also include an attachment section 143 that connects to an access panel 144 extending outside of the internal compartment 124 to enable easier access to the PCO unit 120 (see FIG. 2).

Figure 6:
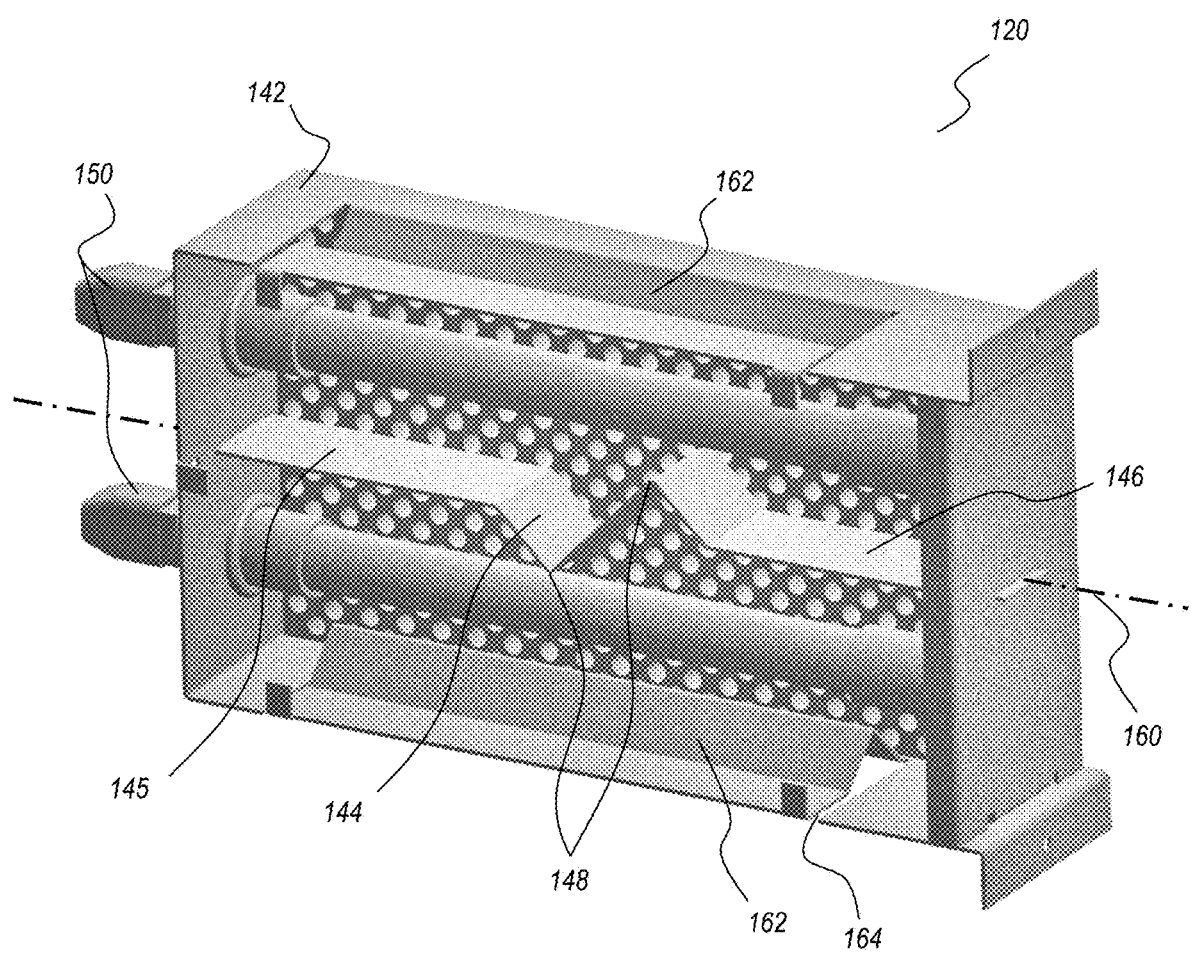
FIG. 6 further illustrates the PCO unit, with portions removed to better show certain internal features of the PCO unit.

FIG. 6 illustrates a view of the PCO unit 120 with one of the photocatalytic cell panels removed to better illustrate the internal components of the PCO unit 120. As shown, the PCO unit 120 preferably includes multiple ultraviolet lamps 150. The multiple lamps 150 may be arranged in a vertically "stacked" fashion, such that each lamp is arranged along a plane that is substantially parallel to the cell panels 140 and that is substantially parallel to a longitudinal axis 160 of the unit. Each ultraviolet lamp 150 may extend horizontally along lines that are transverse or substantially perpendicular to the airflow path (i.e., along the longitudinal axis of the unit 120). Although two lamps 150 are shown here, other embodiments may include more than two lamps 150, such as three, four, five, or more such lamps 150.

The PCO unit 120 also includes a medial reflector 146 disposed between first and second ultraviolet lamps 150 and that extends, as with the lamps 150, in a direction substantially parallel to the longitudinal axis. The medial reflector 146 is configured to reflect light from each of the ultraviolet lamps 150 so that the reflected light has a greater likelihood of impinging upon the photocatalytic surfaces of the cell panels 140. Even though the medial reflector 146 is disposed between the lamps 150 and thus blocks some of the light from each lamp 150 from reaching portions of the photocatalytic surfaces near the opposite lamp 150, it has been surprisingly found that the overall photocatalytic activity of the unit 120 is enhanced by using the medial reflector 146.

The medial reflector 146 also includes a base surface 145 and an angled feature 144 that extends from the base surface 143 at an angle. For example, as shown, the base surface 145 may be substantially parallel with the longitudinal axis, whereas the angled feature 144 includes one or more angled surfaces that each may extend in a direction transverse to the longitudinal axis. Providing such an angled feature 144 has been found to aid in diffusing and reflecting the ultraviolet light in a manner that provides better interaction with the photocatalytic surfaces of the cell panels 140 and thereby further increase the overall photocatalytic activity of the device.

The angled feature 144 includes one or more apexes 148 (i.e., the portions that extend the furthest from the base surface 145). As shown, the apexes may extend along a direction that is transverse to (i.e., substantially perpendicular to) the longitudinal axis 160. The medial reflector 146 may therefore be formed as a strip of metal or other suitable material that is formed/folded to create the angled feature 144. This configuration has been found to be easily manufacturable yet functionally effective in enhancing photocatalytic activity of the device. The medial reflector 146 is also readily integrated into the frame 142 by inserting into the sidewalls of the frame 142. Embodiments having more than two ultraviolet lamps 150 may include multiple medial reflectors (e.g., between each pair of lamps 150).

The PCO unit 120 may also include one or more outer reflectors 162. The outer reflectors 162 may be formed, for example, as part of the frame 142 on upper and/or lower sides. The outer reflectors 162 may extend inward toward the interior chamber of the PCO unit 120 and toward the ultraviolet lamps 150. As with the medial reflector 146, the outer reflectors 162 provide angled surfaces that function to reflect ultraviolet light and thereby better direct the light to the photocatalytic surfaces of the cell panels 140. The outer reflectors 162 may be formed by placing cutouts 164 in the frame 142, which allows the outer reflectors 162 to be readily formed by folding into the desired angled shape.

In contrast to the medial reflector 146, the outer reflectors 162 have apexes (i.e., the inward-most portion) that extend in a direction substantially parallel to the longitudinal axis 160. The combination of at least one outer reflector 162, with apex that runs in a substantially longitudinal direction, and a medial reflector 146, with one or more apexes that run in a direction transverse to the longitudinal axis 160, has been found to provide effective overall reflection of ultraviolet light within the interior chamber of the PCO unit 120 and thereby enhance the photocatalytic activity and efficiency of the PCO unit 120.

From the perspective of the upper ultraviolet lamp 150, for example, the nearby outer reflector 162 on the upper side of the frame 142 includes angled surfaces that help reflect and direct light in "forward" and "backward" directions, as well as "up" and "down," while the medial reflector 146 includes angled surfaces that help reflect and direct light in "left" and "right" longitudinal directions as well as "up" and "down." The combination of reflective surfaces provides an overall configuration that effectively aids in directing the light onto the photocatalytic surfaces for effective photocatalytic activity.

In operation, the lamps 150 are energized and emit ultraviolet radiation toward catalytic surfaces of the cell panels 140, thereby generating oxidizers. The oxidizers are then mixed with the passing air to provide sanitation of the passing air. Preferably, at least some of the oxidizers pass out of and beyond the device 100 with the passing air.

The cell panels 140 include a photocatalyst coating. The photocatalyst coating is placed at least on the inside surface of the cell panels 140 facing the ultraviolet lamps 150. Preferably, the photocatalyst coating also extends into the apertures of the cell panels 140 to coat the surfaces of the apertures. The photocatalyst coating may comprise a metal oxide such as titanium oxide and may optionally include one or more transition metals and/or alloys of transition metals. Examples of additional or alternative photocatalytic materials that may be utilized in the coating include graphene oxide, metal-organic frameworks (MOFs), other semiconductor materials, quantum dots, tantalite, other oxides (e.g., zinc, copper, iron, cadmium, tin, zirconium, or gallium oxide), sulfides (e.g., zinc sulfide), silica, and combinations thereof.

Oxidizers generated during operation of the device may include, for example, hydrogen peroxides, hydroxides, free oxygen molecules, super oxide ions, and ozone. Preferably, however, the PCO unit 120 is configured so that ozone generation is limited or eliminated. While ozone is a powerful oxidizing agent, excess ozone may cause respiratory irritation in sensitive individuals. It has been found that by tailoring the PCO unit 120 to generate effective levels of oxidizers while minimizing or eliminating ozone, effective purification performance is maintained without the potential detrimental effects related to excess ozone.

In order to provide these performance characteristics, the ultraviolet lamps 150 preferably emit light with a wavelength of about 185 to 254 nm. The lamps 150 will typically be rated at about 3 to 20 watts, or more preferably about 5 to 10 watts. Using a lamp 150 with a rating within the foregoing ranges has been found to effectively balance the need to provide sufficient energy for achieving needed photocatalytic activity without creating excessive power inefficiencies and/or taking up too much space.

The structural configuration of the PCO unit 120 is designed to provide effective photocatalytic activity, effective interaction between the airflow and the generated oxidizers, and effective overall volumetric airflow within the size constraints of the air purification device 100. These functions interact with one other, and enhancing one of these functions may involve tradeoffs with one or more of the other functions.

For example, photocatalytic activity may be enhanced by increasing the overall surface area of the ultraviolet lamp(s) (e.g., using a bigger lamp) and/or by increasing the proportion of photocatalytic material within the airflow path. However, either of these changes will also likely increase the airflow resistance of the device, thus lowering the volumetric airflow or requiring more power to maintain higher pressures across the device. In addition, because the size of the airflow path is dictated by the size of the overall air purification device 100, which is desirable to keep within reasonable limits, the overall airflow path size cannot simply be made larger indefinitely. When airflow through the PCO unit 120 is restricted, however, the air turnover rate for the targeted environment is reduced, meaning it takes longer to purify the air and/or meaning air purification effectiveness is reduced.

Similarly, airflow may be increased by limiting the contact between the air and the photocatalytic material, such as by simply passing the air over a photocatalyst rather than through multiple apertures or by increasing the size of the apertures. However, this limits the interaction between the air and the generated oxidizers, which limits the mixing and distribution of the oxidizers within the air. For a given level of generated oxidizers, the oxidizers are therefore less likely to contact and treat the contaminants. Likewise, airflow may be increased by enlarging the spacing between the ultraviolet lamps 150 and the cell panels 140 and/or by reducing the overall surface area of the ultraviolet lamps 150, but this tends to lower the overall photocatalytic generation of oxidizers.

Smaller apertures will tend to restrict airflow to a greater degree than larger apertures. However, because the coated inner surfaces of the apertures may provide a significant portion of the photocatalytic activity of the device, and because smaller apertures allow for a greater overall area of active photocatalytic surfaces, smaller apertures tend to provide greater photocatalytic activity.

It has been found that setting the average cross-sectional area of each aperture at greater than about 0.1 mm$^2$ but less than about 10 mm$^2$ provides effective photocatalytic activity without overly restricting airflow. The apertures may more preferably be sized with an average cross-sectional area of about 0.2 mm$^2$ to about 5 mm$^2$, or about 0.3 mm$^2$ to about 1 mm$^2$. Apertures that are too small tend to reduce overall performance of the device by overly restricting airflow, while apertures that are too large tend to reduce overall performance of the device by overly limiting photocatalytic activity.

The number of apertures included in the cell panel 140 may be varied. Preferably, apertures are provided at a number such that about 25% to about 75% of the plan-view surface area of the cell panel 140 is made up of the apertures, or more preferably about 35% to about 65%, or about 40% to about 60% of the plan-view surface area of the cell panel 140 is made up of the apertures. The "plan-view surface area" refers to the two-dimensional surface area of the upper surface of the cell panel 140 if laid flat and viewed from above.

The width of the cell panels 140 may also be varied. Wider cell panels provide longer apertures with greater overall surface area, and thus provide greater photocatalytic activity, but also increase the length through which the air must pass through the apertures and thus increases airflow resistance.

A "cell fraction" is defined herein as the combined width of the cell panels 140 divided by the overall width between the cell panels 140 (from outer surface to outer surface). The PCO unit 120 may be configured with a cell fraction of about 0.2 to about 0.7, more preferably about 0.3 to about 0.6, and even more preferably about 0.4 to about 0.5. Setting the cell fraction within the foregoing ranges was found to provide improved overall performance of the PCO unit 120.

The distance between the lamps 150 and the inner surfaces of the cell panels 140 may also be varied by adjusting the diameter of the lamps 150 and/or by adjusting the distance between the cell panels 140. A greater distance between the lamps 150 and the cell panels 140 allows greater residence time for air passing through the PCO unit 120, but also reduces the photocatalytic activity by increasing the distance between the lamps 150 and the cell panels 140.

A "light fraction" is defined herein as the width/diameter of one of the lamps 150 divided by the overall distance between inner surfaces of the opposing cell panels 140. The PCO unit 120 may be configured with a light fraction of about 0.45 to about 0.7, or more preferably about 0.5 to about 0.6. Setting the PCO unit 120 so that the light fraction was within the foregoing ranges was found to provide improved overall performance.

The following description provides some additional dimensions of an exemplary PCO unit 120 that has been found to provide effective performance in several applications, particularly in applications involving modular, moveable room cleaning devices such as described herein. It will be understood, however, that the exemplary dimensions are not necessarily limiting, and that other embodiments may be resized or scaled to provide particular application needs.

In one embodiment, the PCO unit 120 may have an overall height of about 2 to 4.5 inches (about 5.1 cm to 114 cm), an overall width of about 1.5 to 2.5 inches (about 3.8 to 6.4 cm), and a length of about 4 to 8 inches (about 10 to 20 cm). The cell panels 140 may be sized to fit accordingly, and may have a width of about 5 mm to about 30 mm, or more preferably about 10 mm to about 20 mm, or even more preferably about 10 mm to about 15 mm. The ultraviolet lamps 150 may also be sized accordingly to fit within the overall dimensions of the device 100, and thus may have a length of about 3 to 7 inches (about 8 to 18 cm), and a diameter of about 0.25 inches to about 0.75 inches (about 0.6 to 2 cm).

Examples

An air purification device was placed in a room having a size of about 1,000 ft² to test the ability to reduce airborne pathogens in the room. Levels of various airborne pathogens were initially tested to establish baseline levels, and then the air purification device began operation. Levels of the same airborne pathogens were tested again at 30 minutes and 60 minutes after beginning operation. Reduction of the airborne contaminants is summarized below in Table 1.

TABLE 1

Percent Reductions in Airborne Pathogens

| Airborne Pathogen | Percent Reduction after 30 minutes | Percent Reduction after 60 minutes |
|---|---|---|
| *Staphylococcus epidermidis* (gram positive bacteria) | 99.99 (4 log) | 99.9999 (6 log) |
| *Erwinia herbicola* (gram negative bacteria) | 99.99 (4 log) | 99.999 (5 log) |
| *Aspergillus niger* (mold spores) | 99.9 (3 log) | 99.99 (4 log) |
| *Bacillus globigi* (mold spores) | 99.9 (3 log) | 99.99 (4 log) |
| MS2 Bacteriophage Virus (RNA virus) | 99.999 (5 log) | 99.9999 (6 log) |
| Phi-X147 Bacteriophage Virus (DNA virus) | 99.99 (4 log) | 99.995% (4.5 log) |

The data summarized above illustrates that the air purification device was capable of reducing several different types of airborne pathogens, common in medical environments, by at least a one or two log reduction, and more typically even by at least a three log reduction, or at least a four log reduction, and up to a 6 log reduction, in a matter of about 30 minutes to about 60 minutes.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An air purification device, comprising:
   a frame having an air inlet and an air outlet;
   a fan assembly configured to move air into the inlet, through an airflow path within an internal compartment of the frame, and out the outlet; and
   a photocatalytic oxidation unit disposed at least partially within the airflow path, the photocatalytic oxidation unit having a longitudinal axis that is transverse to the airflow path, and the photocatalytic oxidation unit including:
      at least one photocatalytic cell panel extending along the longitudinal axis,
      first and second ultraviolet lamps extending along the longitudinal axis and configured to emanate ultraviolet light toward the at least one photocatalytic cell panel, and
      a medial reflector disposed within the photocatalytic oxidation unit between the first and second ultraviolet lamps, wherein the reflector comprises a base surface and an angled feature with a first section that extends from the base surface at an angle in a first direction toward the first ultraviolet lamp and a second section that extends from the base surface at an angle in a second, opposite direction toward the second ultraviolet lamp.

2. The device of claim 1, wherein the first and second ultraviolet lamps are oriented so as to both lie along a plane that is substantially parallel to the at least one photocatalytic cell panel.

3. The device of claim 1, wherein the photocatalytic oxidation unit comprises first and second photocatalytic cell panels disposed on either side of the first and second ultraviolet lamps and each extending along the longitudinal axis.

4. The device of claim 1, wherein the first and second ultraviolet lamps are each positioned on a plane that is substantially parallel to the at least one photocatalytic cell panel.

5. The device of claim 1, wherein the angled feature comprises:
   a first apex corresponding to the first section of the angled feature, the first apex being the closest portion of the medial reflector to the first ultraviolet lamp; and
   a second apex corresponding to the second section of the angled feature, the second apex being the closest portion of the medial reflector to the second ultraviolet lamp;
   wherein both the first and second apexes extend along a direction transverse to the longitudinal axis.

6. The device of claim 5, wherein the first and second apexes of the angled feature extend along a direction that is substantially perpendicular to the longitudinal axis.

7. The device of claim 1, wherein the photocatalytic oxidation unit further comprises a frame, the frame including a first outer reflector positioned on an outer side of the first ultraviolet lamp and extending inwards toward the first ultraviolet lamp.

8. The device of claim 7, wherein the first outer reflector includes an apex that extends in a direction substantially parallel to the longitudinal axis.

9. The device of claim 8, wherein the frame further comprises a second outer reflector positioned on an outer side of the second ultraviolet lamp and extending inwards toward the second ultraviolet lamp.

10. The device of claim 9, wherein the second outer reflector includes an apex that extends in a direction substantially parallel to the longitudinal axis.

11. The device of claim 1, wherein the photocatalytic oxidation unit is disposed with the longitudinal axis substantially perpendicular to the airflow path.

12. The device of claim 1, wherein the fan assembly comprises a centrifugal fan.

13. The device of claim 12, wherein an axis of the centrifugal fan is substantially perpendicular to the airflow path.

14. The device of claim 1, wherein the fan assembly is disposed downstream of the photocatalytic oxidation unit.

15. The device of claim 1, wherein the frame further comprises a filter compartment configured in size and shape for receiving a filter.

16. The device of claim 15, wherein the filter compartment is disposed between the air inlet and the photocatalytic oxidation unit.

17. An air purification device, comprising:
a frame having an air inlet and an air outlet;
a fan assembly configured to move air into the inlet, through an airflow path within an internal compartment of the frame, and out the outlet; and
a photocatalytic oxidation unit disposed at least partially within the airflow path, the photocatalytic oxidation unit comprising a longitudinal axis substantially perpendicular to the airflow path, the photocatalytic oxidation unit including:
at least one photocatalytic cell panel extending along the longitudinal axis,
first and second ultraviolet lamps extending along the longitudinal axis and configured to emanate ultraviolet light toward the at least one photocatalytic cell panel,
a medial reflector disposed between the first and second ultraviolet lamps, wherein the medial reflector includes a base surface and an angled feature that extends from the base surface at an angle toward one or both of the first and second ultraviolet lamps, the medial reflector comprising one or more apexes, as portions closest to the first or second ultraviolet lamp, each apex extending along a direction transverse to the longitudinal axis, and
a first outer reflector positioned on an outer side of the first ultraviolet lamp and extending inwards toward the first ultraviolet lamp, wherein the first outer reflector includes an apex that extends in a direction substantially parallel to the longitudinal axis.

18. The device of claim 17, wherein the at least one photocatalytic cell panel comprises first and second photocatalytic cell panels disposed on opposite sides of one another with the first and second ultraviolet lamps disposed therebetween.

\* \* \* \* \*